(12) United States Patent
Gustafson

(10) Patent No.: US 6,196,981 B1
(45) Date of Patent: Mar. 6, 2001

(54) FORWARD HEAD POSTURE MEASURING DEVICE

(76) Inventor: Norman P Gustafson, 2508 Collin Rd., Pittsburgh, PA (US) 15235

(*) Notice: Subject to any disclaimer, the term of this patent is extended or adjusted under 35 U.S.C. 154(b) by 0 days.

(21) Appl. No.: 09/340,766

(22) Filed: Jun. 28, 1999

(51) Int. Cl.[7] .................................................. A61B 5/103
(52) U.S. Cl. ............................................................ 600/587
(58) Field of Search .................................. 600/587, 594, 600/595

(56) References Cited

U.S. PATENT DOCUMENTS

| | | | |
|---|---|---|---|
| 2,053,810 | * | 9/1936 | Bisel ...................................... 33/512 |
| 2,818,648 | * | 1/1958 | Jochheim ................................... 33/8 |
| 4,134,213 | * | 1/1979 | Kushmuk ............................... 33/512 |

* cited by examiner

Primary Examiner—Cary O'Connor
Assistant Examiner—Pamela L. Wingood

(57) ABSTRACT

A measuring device that effectively measures the distance that a subject's ear is located from the mid point of the subject's shoulder. The device consists of a shoulder mounted base that is placed on a subject's shoulder by an examiner. Extending vertically from the shoulder mounted base is a vertical tower consisting of two parallel vertical members. An extension bar holder is slidably positioned overlying the vertical tower such that the vertical distance of the ear from the shoulder can be adjustably spanned by the extension bar holder and then locked into place. An extension bar is slidably mounted in the extension bar holder so that the extension bar can span the lateral to medial distance that the lateral shoulder is located from the ear. A measuring bar is mounted in the extension bar that includes a distance scale and an ear position cone so that the anterior distance a subject's ear is located from a subject's shoulder can be quickly and accurately measured.

9 Claims, 4 Drawing Sheets

FORWARD HEAD POSTURE MEASURING DEVICE

BACKGROUND

1. Field of Invention

This Invention relates to a device that quickly and easily measures the distance of forward head posture or positioning of an individual.

2. Description of Prior Art

A position or posture of the head that is forward with respect to the shoulders or midline axis of the body is considered by Physical Therapists and other health care professionals to cause problems with respect to the musculoskeletal system. These problems may include a decreased respiratory capacity and various nerve impingement problems such as Thoracic Outlet Syndrome as well as overstretching of the posterior ligaments. Dentists have also correlated a forward head posture with Temperomandibular joint disorder. (Preston et. al. Journal of Orofacial Pain, Spring 1995 vol. 9, pgs. 161–167).

A method of assessing the magnitude of forward head position that is known is having the subject stand sideways to a printed grid and then using the grid marks to measure various postural distances. A problem with this method with respect to measuring the distance of the ear from the shoulder is that these two points are not co-planar leading to difficulty avoiding measuring errors.

Rutella in U.S. Pat. No. 4,425,713 discloses a device for measuring posture of the whole body. While this device is capable of measuring head and shoulder position, it is not capable of measuring head position with respect to the subjects shoulder. Piscopo, Stetson and Stetson disclose in U.S. Pat. No. 5,469,861 a device that records ultrasonic signals between two postural points to assess human posture. Since all of the aforementioned devices are bulky or expensive, most therapy clinics are currently using visual inspection only to assess forward head posture. There remains, therefore a need for a device that is capable of accurately, easily and inexpensively measuring forward head posture.

OBJECTS AND ADVANTAGES

Accordingly, it is an object of the current invention to provide a device that is capable of accurately measuring forward head posture.

It is another object of this device to measure forward head posture in a short period of time.

It is a further object of the current invention to provide a device that is easily portable.

To accomplish these objectives, the device consists of a shoulder mounted base, a vertical tower, an extension bar holder, an extension bar, a measuring bar including an ear position cone and associated hardware. In typical application, a shoulder mounted base is secured with velcro or other means to the top and lateral region of a subject's shoulder. A vertical tower approximately 8 inches in height mounts on the shoulder mounted base. The vertical tower contains a level to insure vertical alignment of the vertical tower. The vertical tower consists of two parallel upright projections and an overlying top section. The extension bar holder is slidably mounted to the vertical tower, and can be secured to the vertical tower at any desired height using a set screw. The extension bar holder has holes in each end which receive the extension bar. The extension bar is slidably mounted in the extension bar holder such that its length can be adjusted and then secured at the desired length with a hand tightening bolt or maintained in position by shape and coefficient of friction of the communicating surfaces. The extension bar has an opening in its end closest to the subject's head for receiving the measuring bar. The measuring bar is slidably mounted in the extension bar and includes an ear position cone. The measuring bar contains metric and standard measuring unit scales.

DESCRIPTION OF PREFERRED EMBODIMENT

Figure 1:
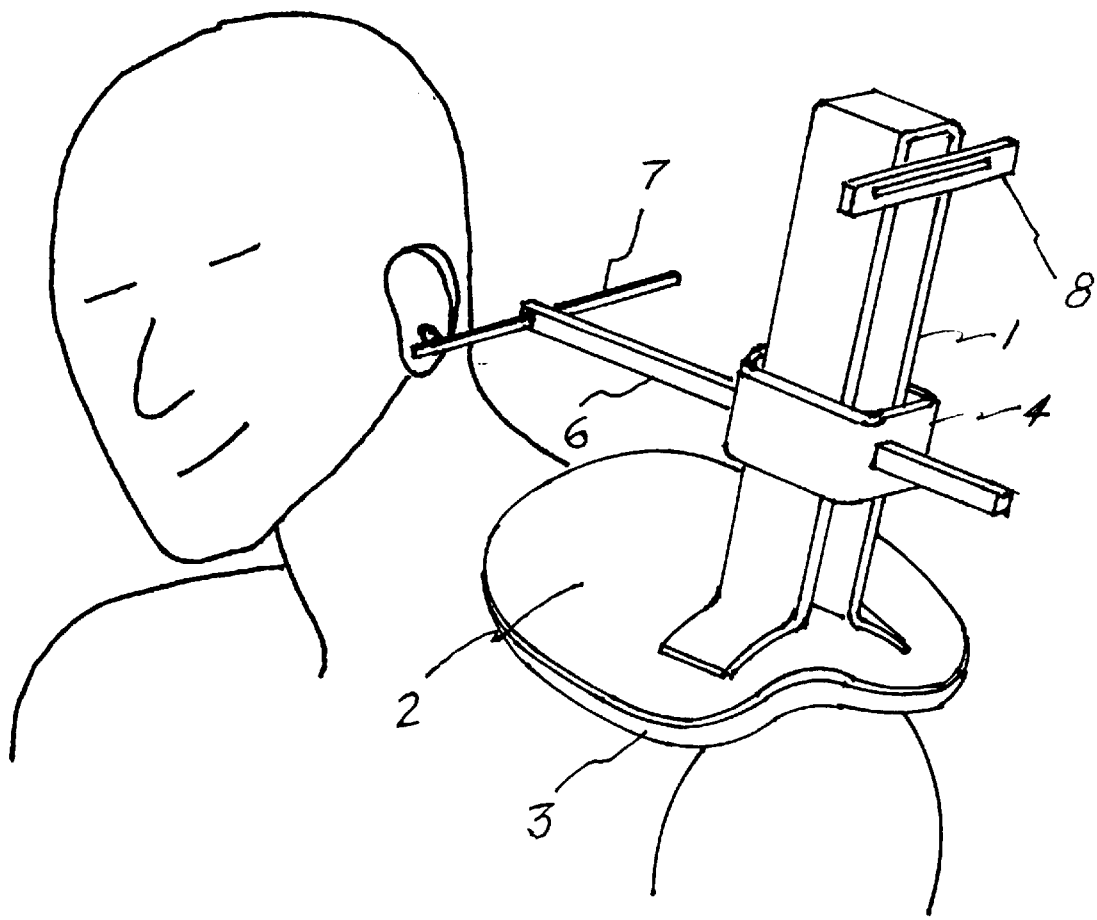
FIG. 1 shows a perspective view of the invention.
Figure 2:
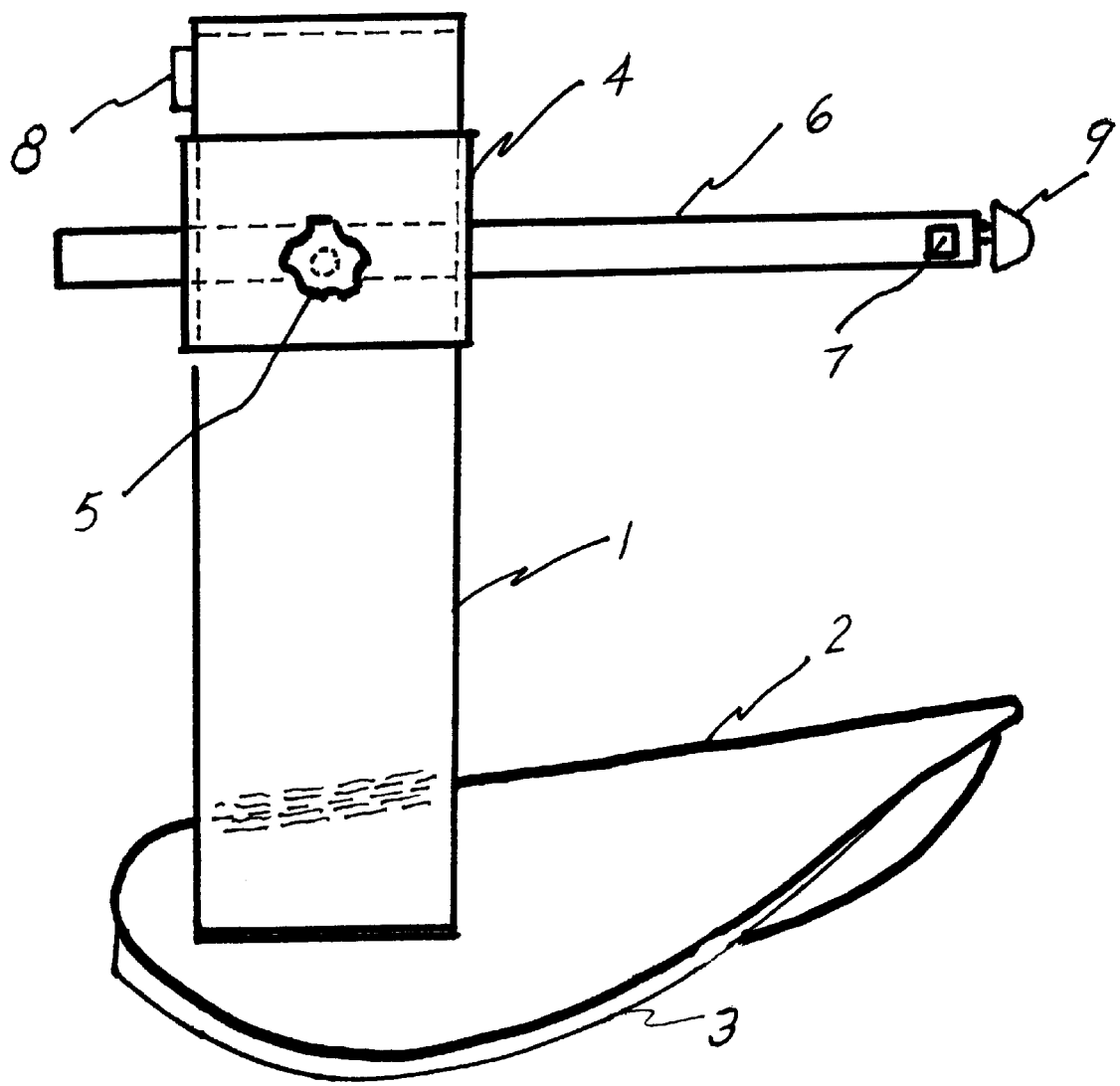
FIG. 2 shows a rear view of the invention.
Figure 3:
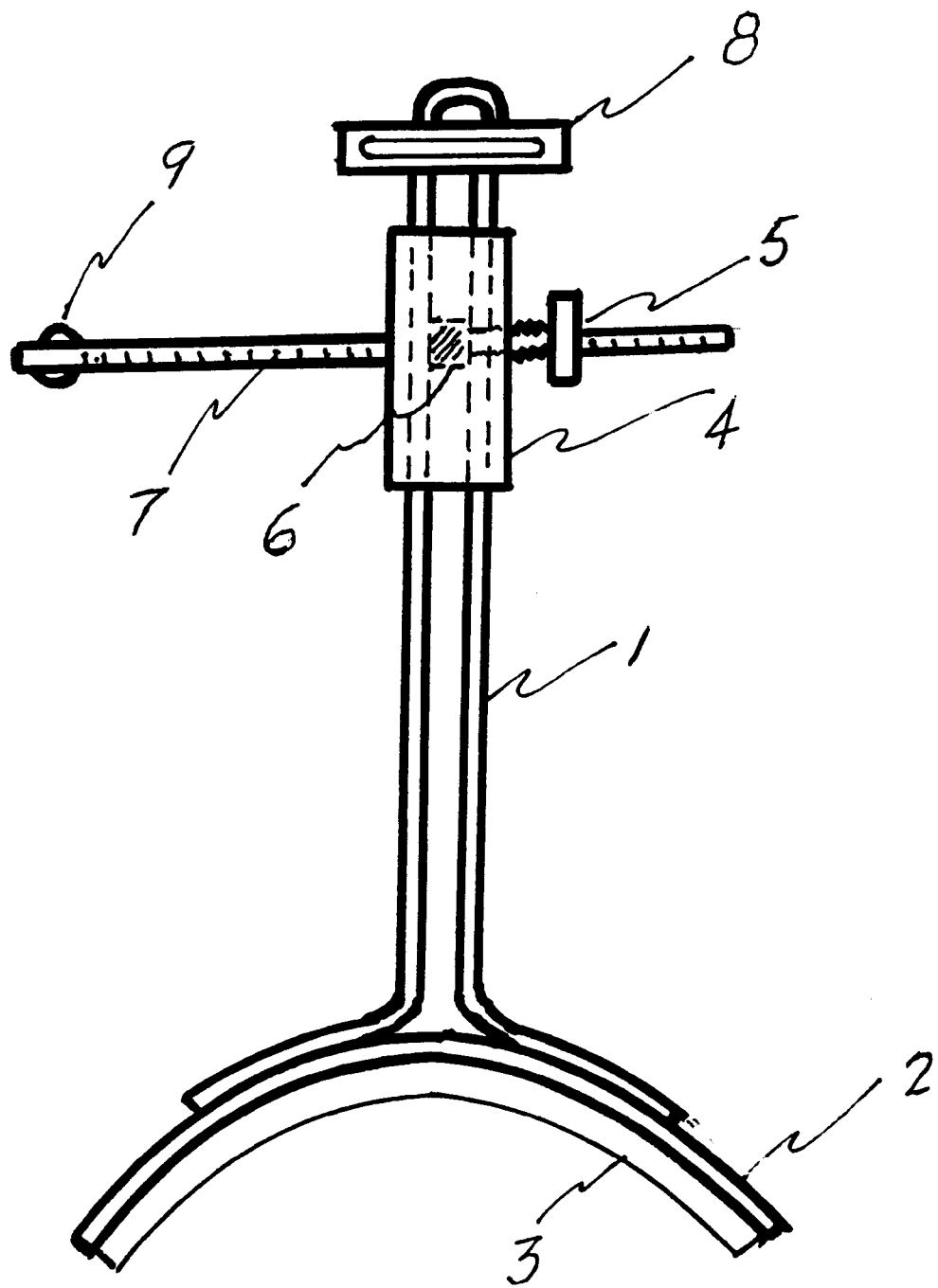
FIG. 3 shows a side view of the invention.
Figure 4:
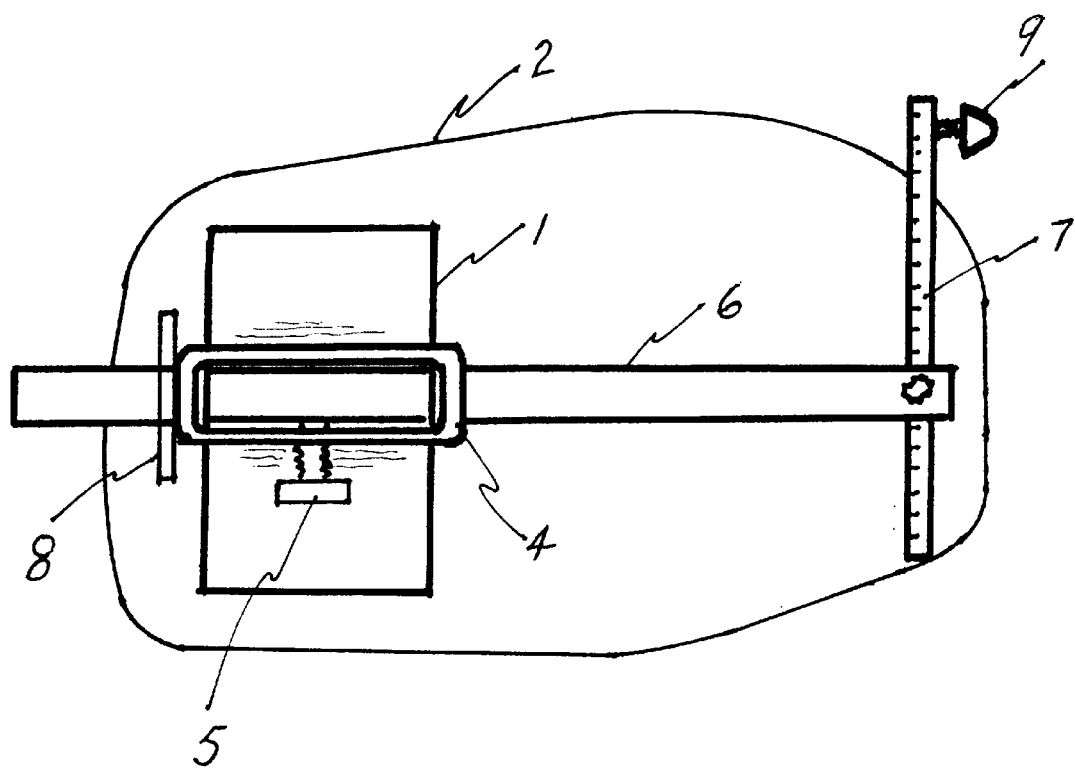
FIG. 4 shows a top view of the invention.

With reference to figures one through four, there is shown a typical embodiment of the current invention A base 2 is of contoured shape concave on the undersurface and is generally shaped to correspond to the contour of an average shaped person's shoulder. Rigidly secured to the undersurface of the base 2 is a foam pad 3. Rigidly attached to the base 2 is a vertical tower 1 which consists of two parallel vertical members. Slidably positioned around the vertical tower 1 is an extension bar holder 4. The extension bar holder 4 includes a threaded hole through which an extensions set screw 5 is mounted. The extension bar holder 4 also contains openings at two of its sides through which an extension bar 6 is slidably mounted. A level 8 is rigidly mounted to the vertical tower 1. The extension bar 6 contains an opening in it's end closest to the ear. A measuring bar 7 is slidably located in this opening. The measuring bar 7 contains a distance scale in inches and centimeters and is oriented at right angles to the extension bar 6. Rigidly attached to the measuring bar 7 is an ear position cone 9. Operation FIGS. 1–4

To measure the forward distance a subjects ear is located with respect to the midline of the body (generally accepted to lie in the middle of the acromion of the shoulder) the examiner places the device on either the left or right shoulders of the subject with the base 2 positioned over the middle of the subject's acromion. The extension bar holder 4 is then raised or lowered so that the extension bar 6 is located at approximately the subject's ear level. The extension bar 6 is then slid toward the subject's ear so that the measuring bar 7 and ear pointer 9 are located at a distance of one inch or less with respect to the subject's ear. The extension bar 6 can then be secured by tightening the set screw 5. The measuring bar is then positioned so that the ear position cone 9 is located adjacent to and points toward the subject's ear canal. The distance the ear position cone is located from the extension bar 5 is read on the scale indicating the forward head position of the subject.

I claim:

1. A forward head posture measuring device comprising:
   a. a shoulder mounted base;
   b. a vertical tower having attachment means for rigidly attaching said vertical tower to said shoulder mounted base and;
   c. an extension bar holder slidably connected to said vertical tower with securing means to rigidly attach said extension bar holder to said vertical tower whereby the vertical distance between a person's shoulder and ear may be spanned by said extension bar holder;
   d. an extension bar slidably connected to said extension bar holder and extending parallel to the longitudinal axis of said base; and e. a measuring bar slidably connected to said extension bar whereby an examiner can measure the anterior distance a person's ear is located with respect to a person's shoulder.

2. The device of claim 1 wherein said shoulder mounted base is of a contoured shape concave on the underside and generally approximating the shape of an average person's lateral shoulder region whereby a stable attachment surface for said vertical tower is provided.

3. The device of claim 2 wherein a foam pad is attached to the undersurface of said shoulder mounted base and said foam pad is of varying thickness such that the lateral section of said shoulder mounted base will rest parallel to the floor when said shoulder mounted base is placed on a standing person's shoulder.

4. The device of claim 1 wherein said extension bar holder is comprised of four joined rectangular sides with openings through two opposite sides to accommodate positioning said extension bar through said openings and allowing sliding of said extension bar within said extension bar holder.

5. The device of claim 1 wherein said extension bar can be slidably moved within said extension bar holder and then maintained in the obtained position by friction surfaces or other securing means.

6. The device of claim 1 wherein said extension bar has an opening at one end shaped so that said measuring bar can be slidably positioned in said extension bar.

7. The device of claim 6 wherein said measuring bar can be slidably moved within said extension bar and then maintained in the obtained desired position by friction surfaces or other securing means.

8. The device of claim 1 wherein a level that allows vertical positioning of said vertical tower is mounted between said vertical members of said vertical tower.

9. The device of claim 1 wherein an ear position cone is rigidly attached to said measuring bar.

* * * * *